United States Patent
Haskell et al.

(10) Patent No.: US 6,378,370 B1
(45) Date of Patent: Apr. 30, 2002

(54) TEMPERATURE COMPENSATED SURFACE-LAUNCHED ACOUSTIC WAVE SENSOR

(75) Inventors: Reichl B. Haskell, Veazie; Joshua J. Caron, Old Town, both of ME (US)

(73) Assignee: Sensor Research & Development Corp., Orono, ME (US)

( * ) Notice: Subject to any disclaimer, the term of this patent is extended or adjusted under 35 U.S.C. 154(b) by 0 days.

(21) Appl. No.: 09/520,509

(22) Filed: Mar. 8, 2000

(51) Int. Cl.[7] ............................................... G01N 29/02
(52) U.S. Cl. .................. 73/579; 73/24.06; 73/61.49; 310/313 B
(58) Field of Search ................ 73/24.01, 24.05, 73/24.06, 597, 54.41, 61.49, 61.79, 64.42, 64.53; 310/313 B

(56) References Cited

U.S. PATENT DOCUMENTS

| | | | |
|---|---|---|---|
| 4,312,228 A | | 1/1982 | Wohltjen ...................... 73/597 |
| RE32,859 E | * | 2/1989 | Marshal et al. ............. 333/151 |
| 4,895,017 A | * | 1/1990 | Pyke et al. ..................... 73/23 |
| 5,012,668 A | * | 5/1991 | Haworth .................... 73/24.06 |
| 5,025,346 A | * | 6/1991 | Tang et al. .................. 361/283 |
| 5,130,257 A | * | 7/1992 | Baer et al. .................. 436/151 |
| 5,325,704 A | * | 7/1994 | Mariani et al. ............ 73/24.06 |
| 5,418,058 A | * | 5/1995 | Li et al. ..................... 428/327 |
| RE35,204 E | * | 4/1996 | Lewis .................... 310/313 A |
| 5,646,584 A | * | 7/1997 | Kondratyev et al. ........ 333/193 |
| 5,817,922 A | * | 10/1998 | Rapp et al. ................. 73/24.06 |
| 5,992,215 A | | 11/1999 | Caron et al. ............... 73/24.01 |
| 6,049,155 A | * | 4/2000 | Graebner et al. ....... 310/313 R |
| 6,198,197 B1 | * | 3/2001 | Yamanouchi et al. ... 310/313 R |

* cited by examiner

*Primary Examiner*—Hezron Williams
*Assistant Examiner*—C D Garber
(74) *Attorney, Agent, or Firm*—Pierce Atwood

(57) ABSTRACT

A method and apparatus for improving temperature stability of surface-launched acoustic wave sensors is described. The system includes a plurality of acoustic wave delay lines or resonators coated with identical films which are physically, chemically, biologically, or otherwise sensitive to one or more target chemical or biological analytes. At least one of the delay lines or resonators, referred to herein as reference channels, is used as a frequency reference to which the oscillation frequencies of the remainder of the delay lines or resonators, referred to as sensing channels, are compared. A thin coating of material that is preferably a passivation layer not sensitive to the analytes, is disposed upon the surface-launched acoustic wave sensor. The passivation layer covers sensing films on the reference channels, blocking or impeding interaction of the sensing films and the analytes thereby. The passivation layer is covered by the sensing films on the sensing channels, allowing interaction between the sensing films and the analytes thereby. All reference and sensing channels are preferably configured as oscillators, whereby effects of temperature fluctuation can be reduced significantly through subtractive combination of the reference and sensing channel oscillation frequencies.

27 Claims, 7 Drawing Sheets

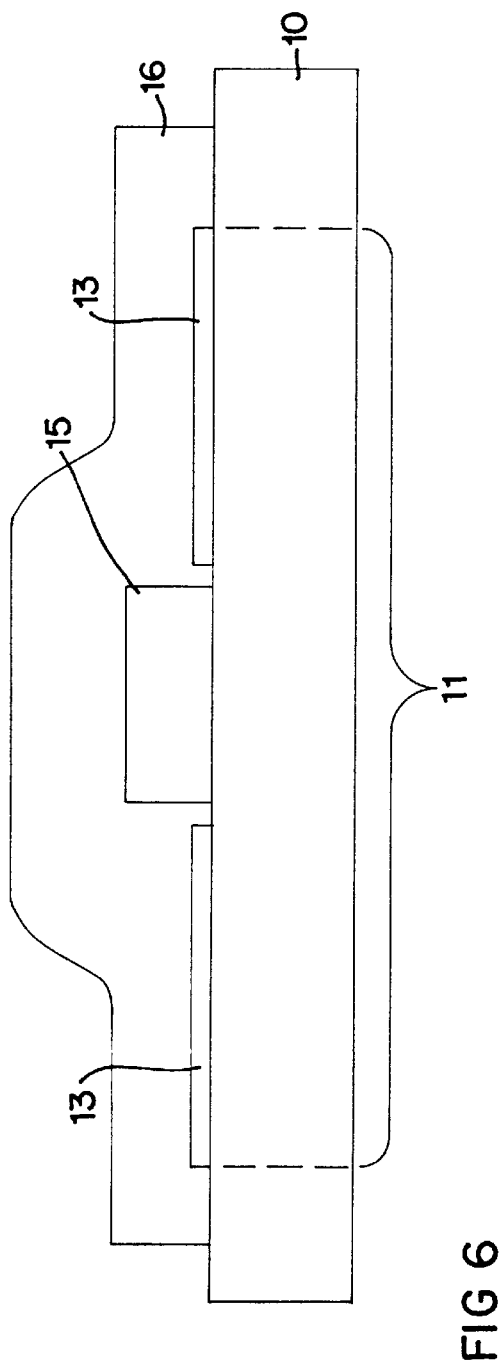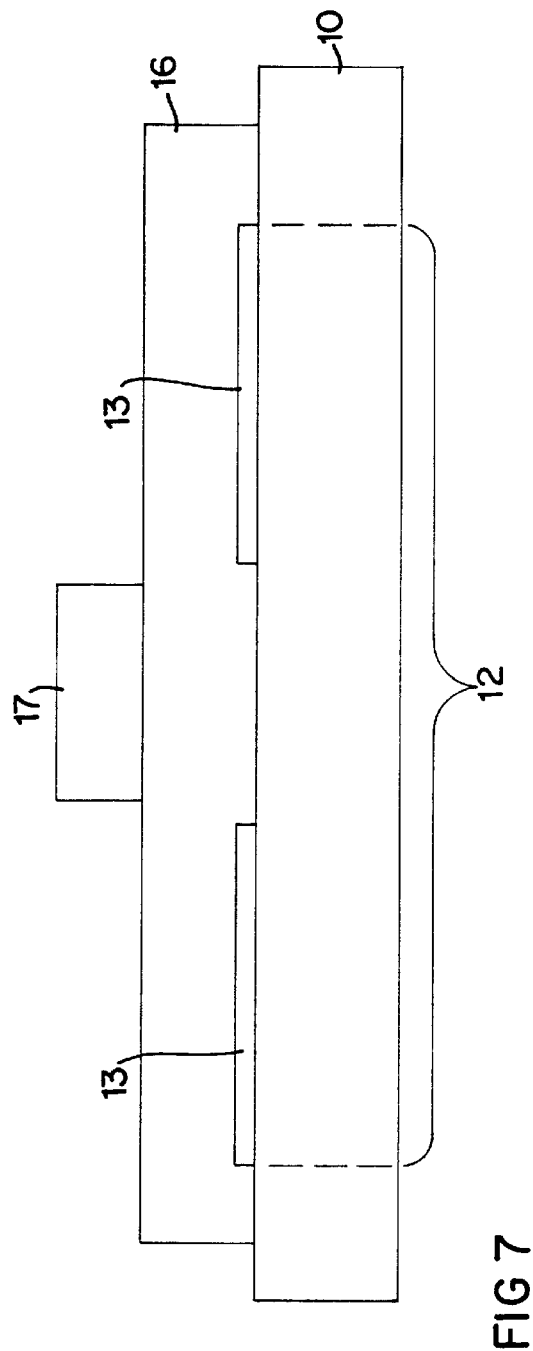

TEMPERATURE COMPENSATED SURFACE-LAUNCHED ACOUSTIC WAVE SENSOR

BACKGROUND OF THE INVENTION

1. Field of the Invention

This invention relates to surface-launched acoustic wave sensors, such as chemical and biological sensors, and more particularly to increased temperature stability thereof.

2. Description of the Prior Art

As is known in the art, surface-launched acoustic wave devices may be utilized to detect and quantify numerous measurands by means of perturbations induced in the electrical and mechanical properties of the devices by those measurands. Surface-launched acoustic wave devices include several specific classes, such as surface acoustic waves (SAW), surface transverse waves (STW), surface skimming bulk waves (SSBW), pseudo-surface acoustic waves (PSAW), acoustic plate modes (APM), Love waves, Lamb waves, and liquid guided acoustic waves (LGAW). Acoustic waves can be generated and measured using interdigital transducers on the surfaces of piezoelectric substrates, such as quartz, lithium niobate, lithium tantalite, etc., whereby an electric potential is converted into a mechanical strain and vice versa. The specific geometry of the substrate and interdigital transducers and the type and crystallographic orientation of the substrate material determine the spectrum of waves that will be excited and measured. Through careful control of these parameters and the environment in which the device is operated, it is usually possible to realize a device that allows the generation, propagation, and detection of only one class of the surface-launched acoustic waves listed above (e.g. SAW).

Because the velocity of an acoustic wave is sensitive to the mechanical and electrical properties of the medium through which it propagates, surface-launched acoustic wave devices can be used as sensors, as taught, for example, by U.S. Pat. No. 4,312,228 as shown in FIG. 1. Velocity of the waves can be measured using a delay line oscillator configuration. This configuration consists of (1) an input interdigital transducer which converts an electrical signal into a mechanical wave, (2) a finite distance, denoted the "delay path", through which the mechanical wave propagates, (3) an output interdigital transducer which converts the mechanical wave back into an electrical signal, and (4) an amplifier which increases the output electrical signal strength and feeds the stronger signal back into the input interdigital transducer. Because of this positive feedback configuration, self-oscillation is sustained at a specific frequency determined primarily by the velocity of the mechanical wave. Therefore, the oscillation frequency can be used as a direct measure of the velocity.

Likewise, an acoustic resonator configuration can be used to measure velocity of the acoustic wave. In this configuration, one or two interdigital transducers are disposed upon a piezoelectric substrate so as to form an acoustic resonant cavity. Using appropriate resonator electronics, an oscillator circuit can be realized, whereby the oscillation frequency thereof can be used as a direct measure of the velocity.

A chemical sensor can be realized by coating the device or (in the case of a delay line) the delay path thereof, with a thin coating which is physically, chemically, biologically, or otherwise sensitive to a target analyte (measurand). Mechanical and electrical perturbations to the thin coating induced by interaction with the target measurand, including changes in surface-bound mass, elasticity, electrical conductivity, and permittivity, alter the acoustic wave velocity and are, therefore, manifested as alterations in the oscillation frequency of the device. Oscillation frequency can then be correlated to concentration or quantity of the target analyte. Hence, a surface-launched acoustic wave sensor is realized.

One of the key limiting factors to the ultimate sensitivity of a surface-launched acoustic wave sensor is noise induced by inevitable temperature fluctuations. Temperature changes induce noise in the sensor's operating frequency for two major reasons. First, the elastic, dielectric, and piezoelectric coefficients of the substrate change with temperature, thereby changing the velocity of the wave and, hence, the oscillation frequency. The magnitude of this effect is called the "temperature coefficient of velocity" (TCV). Second, the substrate grows or shrinks with changing temperature. This changes the distance across which the acoustic wave must propagate, thereby changing the net phase shift through the device. This results in a slight change in resonant frequency to offset the phase shift. The magnitude of this effect is denoted the "thermal expansion coefficient", $\alpha$. The overall temperature sensitivity of the oscillation frequency, or "temperature coefficient of frequency" (TCF), is given as:

$$TCF = TCV - \alpha \qquad (1)$$

The larger the magnitude of TCF, the more sensitive the device is to temperature fluctuations. Two strategies are commonly employed to reduce this temperature noise. The first is to minimize TCF by utilizing a substrate for which TCV and $\alpha$ are exactly equal at some temperature and, hence, subtractively cancel in equation 1. For SAW applications rotated Y-cut quartz is a common example of such a substrate. By varying the rotation angle of the cut, one can choose any temperature over a broad range for which the substrate will be stable. FIG. 2 shows the theoretical variation of normalized oscillation frequency as a function of temperature for 42.75° (also denoted ST cut) and 26° rotated Y-cut quartz. As the figure shows, the oscillation frequency for each of these cuts (and all others in the rotated Y-cut family) demonstrates a parabolic behavior such that frequency increases with increasing temperature up to some "turnover temperature" (the vertex of the parabola), whereby further temperature increases result in a decrease in oscillation frequency. For small temperature variations around the turnover temperature, TCV will balance a in equation 1 above, and frequency fluctuations will be minimized. Again, as shown in the figure, different rotation angles result in different turnover temperatures.

While temperature compensated substrates are used commonly for noise reduction in acoustic wave signal processing applications, where it is desired to maintain a constant frequency at all times, this technique is not as practical for sensor applications. In sensor applications, one typically coats a portion of the acoustically active area of the device with a material that facilitates sensitivity to a target analyte. The very application of this material, however, can dramatically alter the temperature characteristics of the device. For applications where many different film materials are to be used or applications where film parameters such as thickness, viscosity, electrical conductivity, or density may change over time, it is often impractical or impossible to maintain adequate temperature stability.

The second strategy commonly used to reduce temperature noise is the "dual" configuration, where a reference oscillator (channel) is used in tandem with the sensing channel, as taught, for example, in U.S. Pat. No. 5,992,215 as shown in FIG. 3. The reference channel is located on the same substrate and is designed to be exactly the same as the sensing channel, but without the sensing film (coating). The oscillation frequency of this reference is then subtracted from that of the sensing channel. Temperature fluctuations that affect both channels equally are, therefore, cancelled through subtraction. Ideally, this results in a signal that is dependent only on changes in the sensing film.

However, in reality this is not the case. As described above, the addition of any perturbation to an acoustic device (including a sensing film) can dramatically affect the TCF. Therefore, temperature will not have the same effect on the sensing channel as it does on the reference channel, and the temperature noise will not be cancelled out. In some cases, it can even be made worse. For example, FIG. 4 shows the theoretical difference in oscillation frequency for two surface acoustic wave devices on the same substrate (24° rotated Y-cut quartz) as a function of temperature. The only difference between the two devices is the addition of a thin metal film on one. As shown in the figure, however, this film has a striking impact on the temperature sensitivity of the device. Hence, the difference frequency of such a dual setup would still be highly temperature sensitive, defeating the whole purpose of this strategy.

SUMMARY OF THE INVENTION

It is therefore an object of the present invention to mitigate temperature-induced measurement noise in surface-launched acoustic wave sensors with a novel strategy for matching the temperature characteristics of two or more delay lines or resonators, one being sensitive to a target analyte and the other acting as a reference to which the former is compared.

According to one embodiment of the present invention, the above is accomplished by utilizing an impermeable layer of chemically inert material on both channels. On the sensing channels, this impermeable passivation layer is deposited beneath the sensing films and, therefore, has essentially no effect on the chemical sensitivity of the device. On the reference channel, however, the passivation layer is deposited on top of a sensing film identical to that on the sensing delay line, thus rendering that film insensitive. Because both delay lines contain the same two films, albeit in different orders from top to bottom, the temperature characteristics of the two delay lines are essentially identical. This remains true for any number of films in any order, as long as the cumulative thickness of the films is less than the acoustic wavelength (typically tens of microns). Thus, this invention is based on the principle that the order in which different thin films are deposited upon a surface-launched acoustic wave delay line has virtually no bearing on the temperature characteristics of that delay line, but it plays a pivotal role in determining the chemical sensitivity of the device.

According to another embodiment of the invention, the impermeable passivation layer is extended to cover the entire acoustically active portion of each interdigital transducer. This impedes oxidation and other chemical changes to the metal interdigital transducers, thereby reducing long-term drift of the oscillation frequency. Electrical contact to the interdigital transducers is then made by extending the bus bars away from the acoustically active area.

In a third embodiment of the invention, one or more serpentine resistive metal strips are added to the device in order to precisely measure temperature at the surface of the device. The passivation layer is extended to cover this resistive thermal device (RTD), thereby eliminating long-term drift in the resistance due to oxidation and other chemical interactions. By coupling this device with a heater and using the RTD for temperature feedback, temperature of the device can be controlled very accurately, further reducing temperature-induced noise in the oscillation signal. This embodiment of the invention may be used in a SAW dual delay line sensor arrangement on a quartz substrate, with gold as the sensing film and glass ($SiO_2$) as the passivation layer.

BRIEF DESCRIPTION OF THE DRAWINGS

FIG. 6 illustrates the structure of the reference delay line of the present invention from a cross-sectional view;

FIG. 7 illustrates the structure of the sensing delay line of the present invention from a cross-sectional view.

DETAILED DESCRIPTION OF THE PREFERRED EMBODIMENTS OF THE INVENTION

Figure 1:
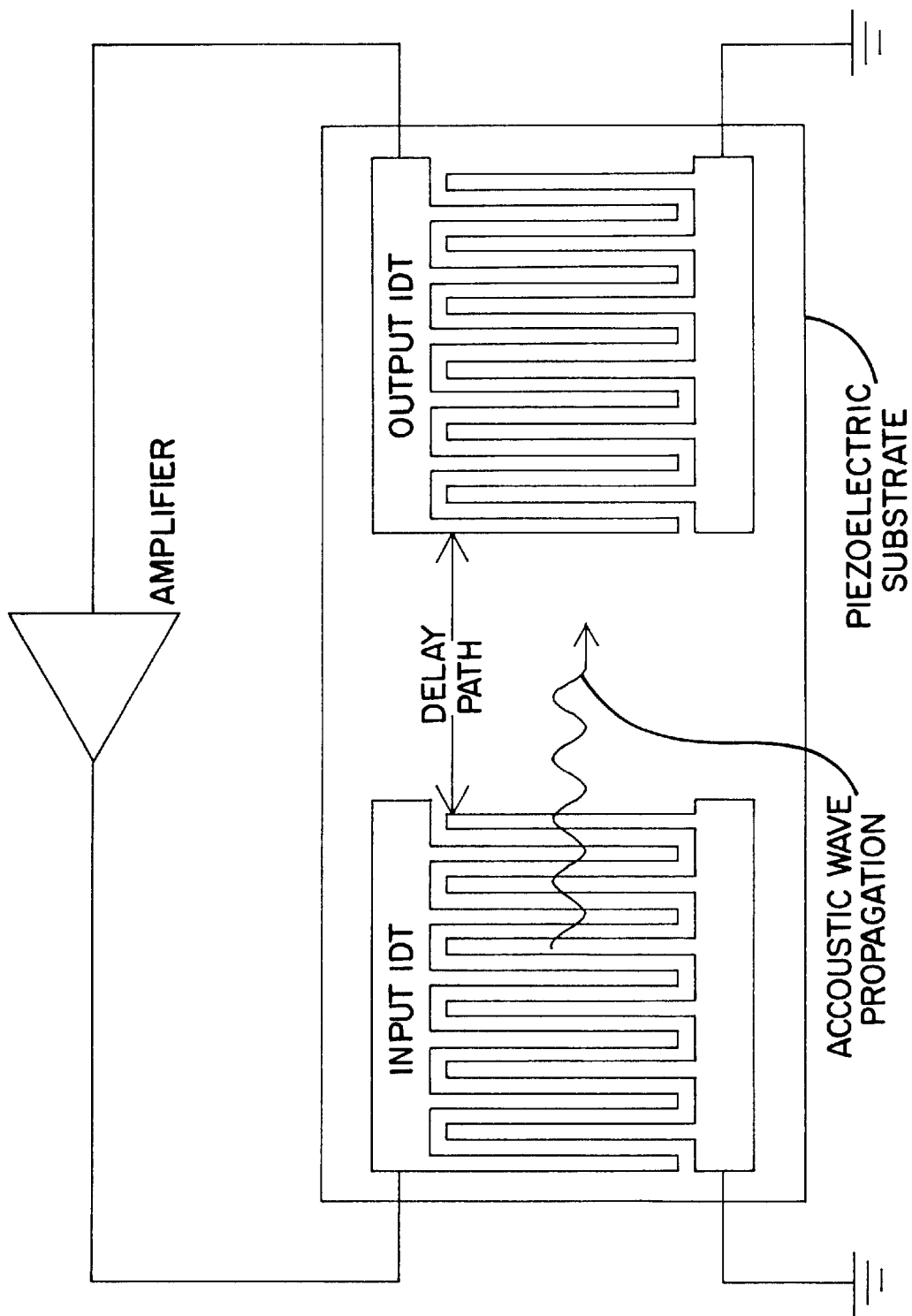
FIG. 1 is a simplified schematic block diagram of the delay line oscillator configuration of the prior art.
Figure 2:
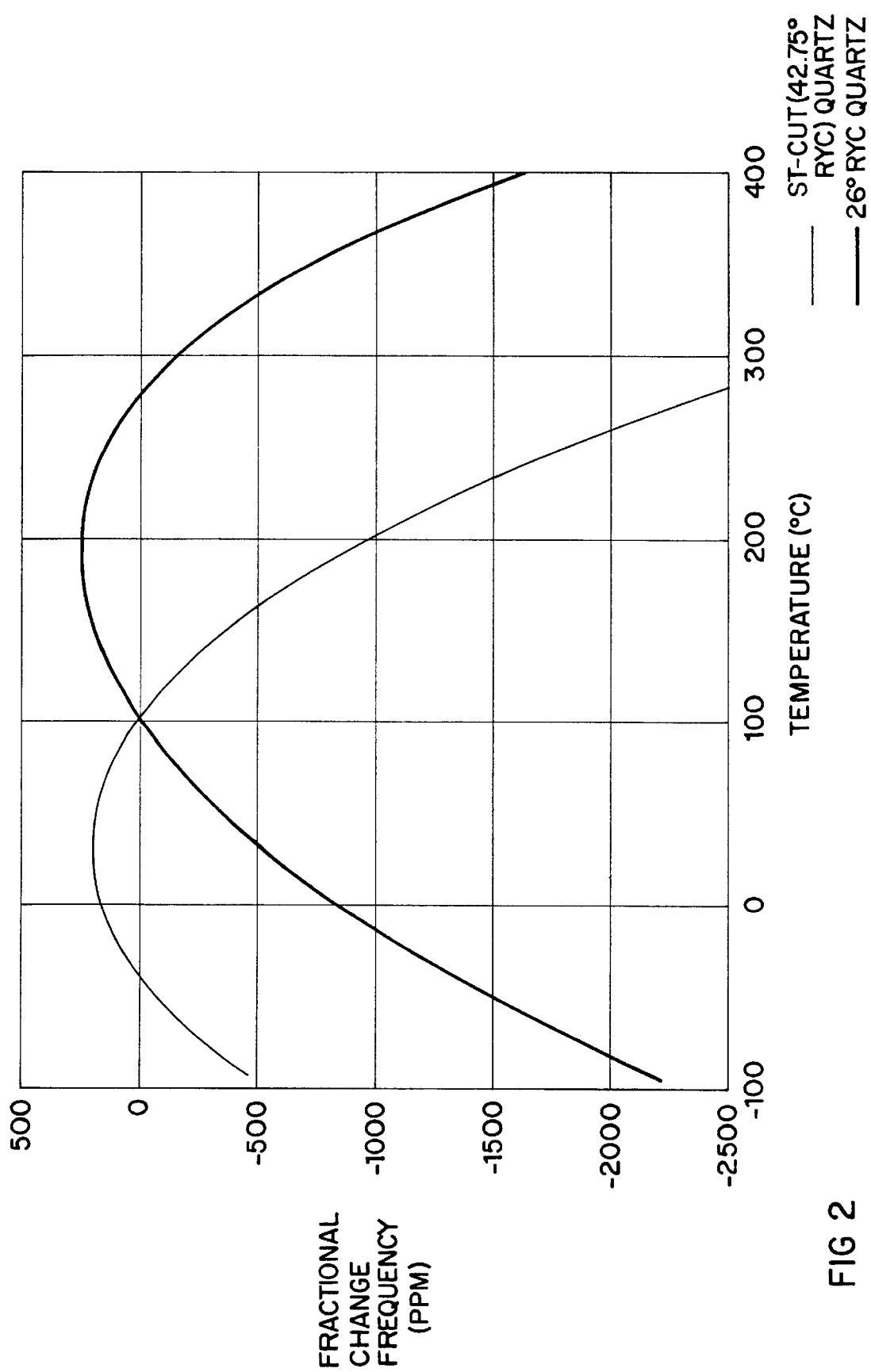
FIG. 2 shows a plot of the oscillation frequency of a surface acoustic wave oscillator of the prior art with changing temperature for two rotated Y-cuts of quartz.
Figure 3:
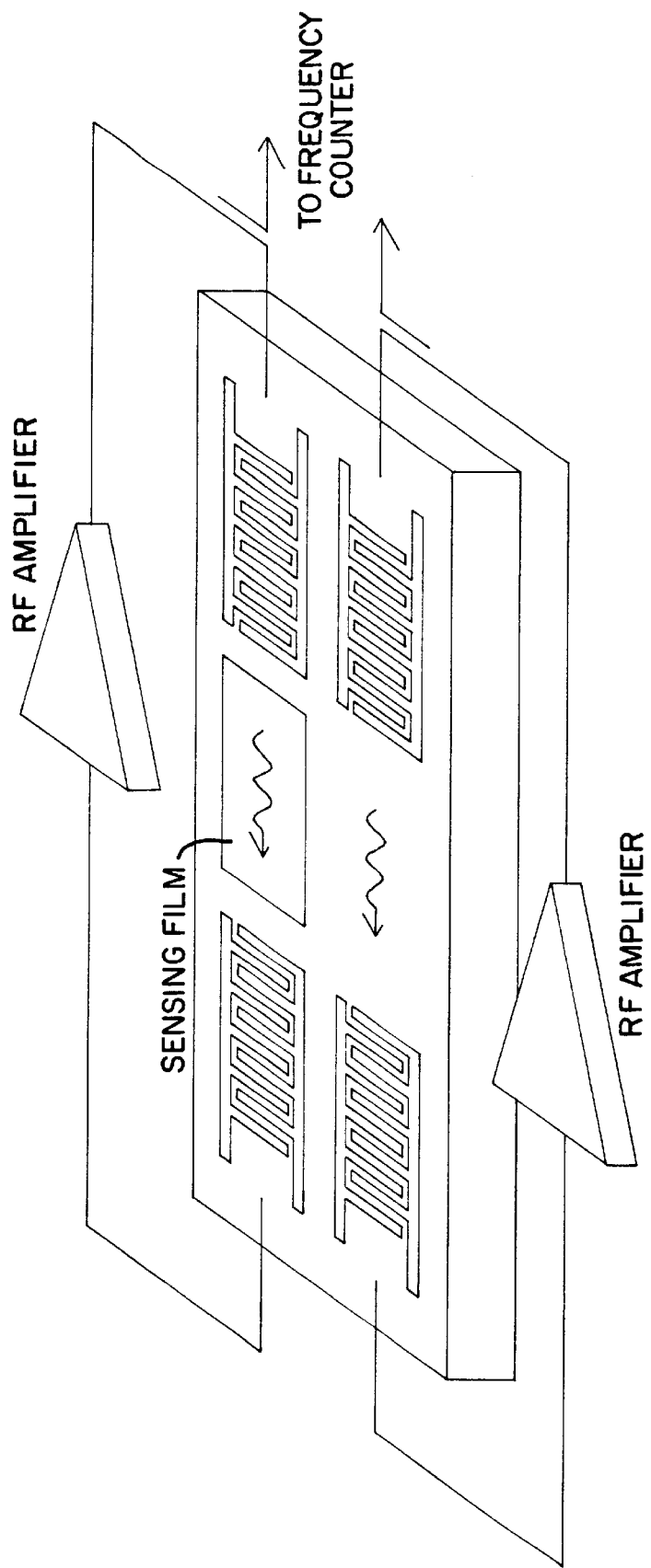
FIG. 3 shows an illustration of the dual delay line oscillator configuration of the prior art.
Figure 4:
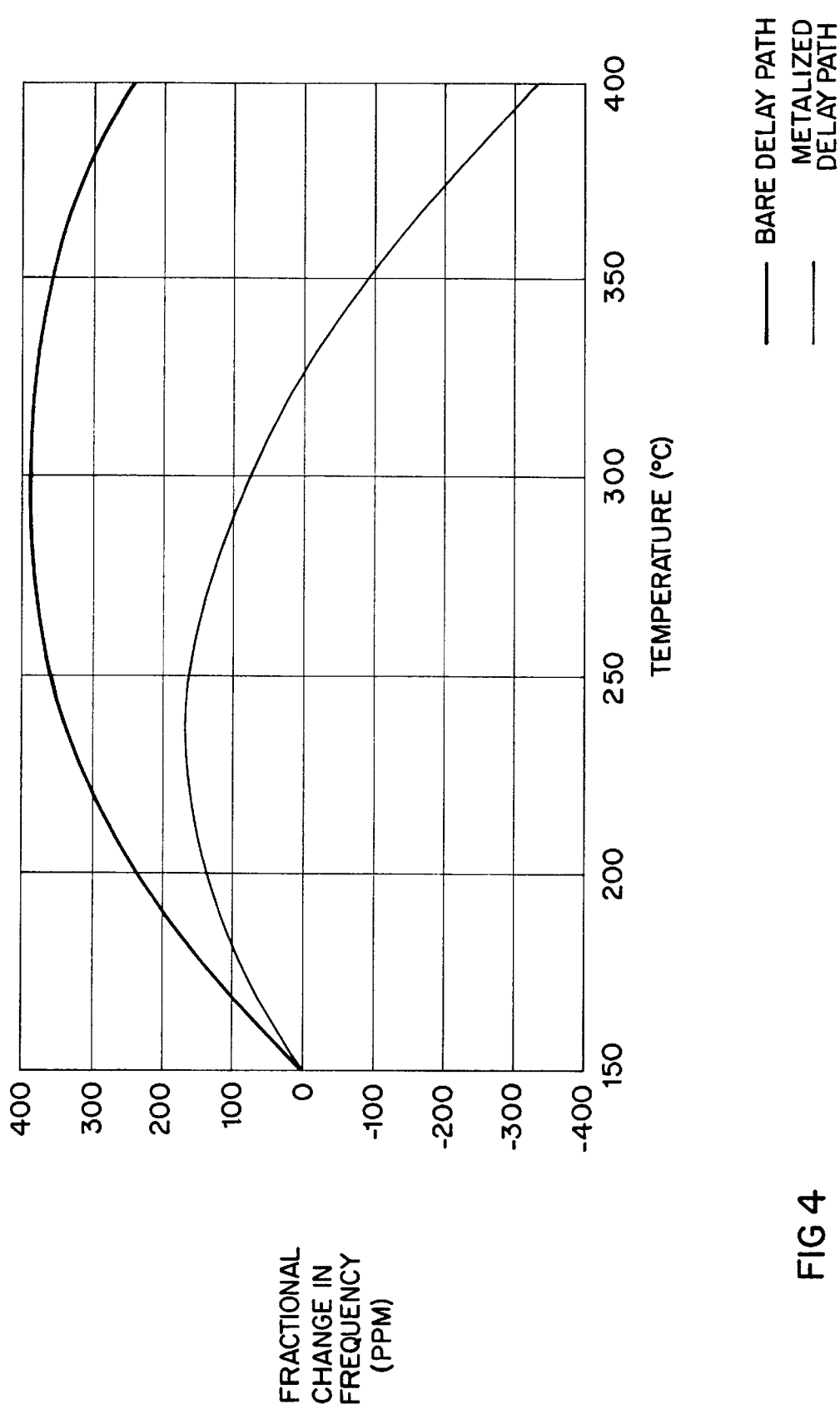
FIG. 4 shows a plot of the oscillation frequency of a surface acoustic wave oscillator of the prior art with changing temperature for films 24° rotated Y-cut quartz with and without a thin aluminum film with a thickness equal to 1% of the acoustic wavelength.
Figure 5:
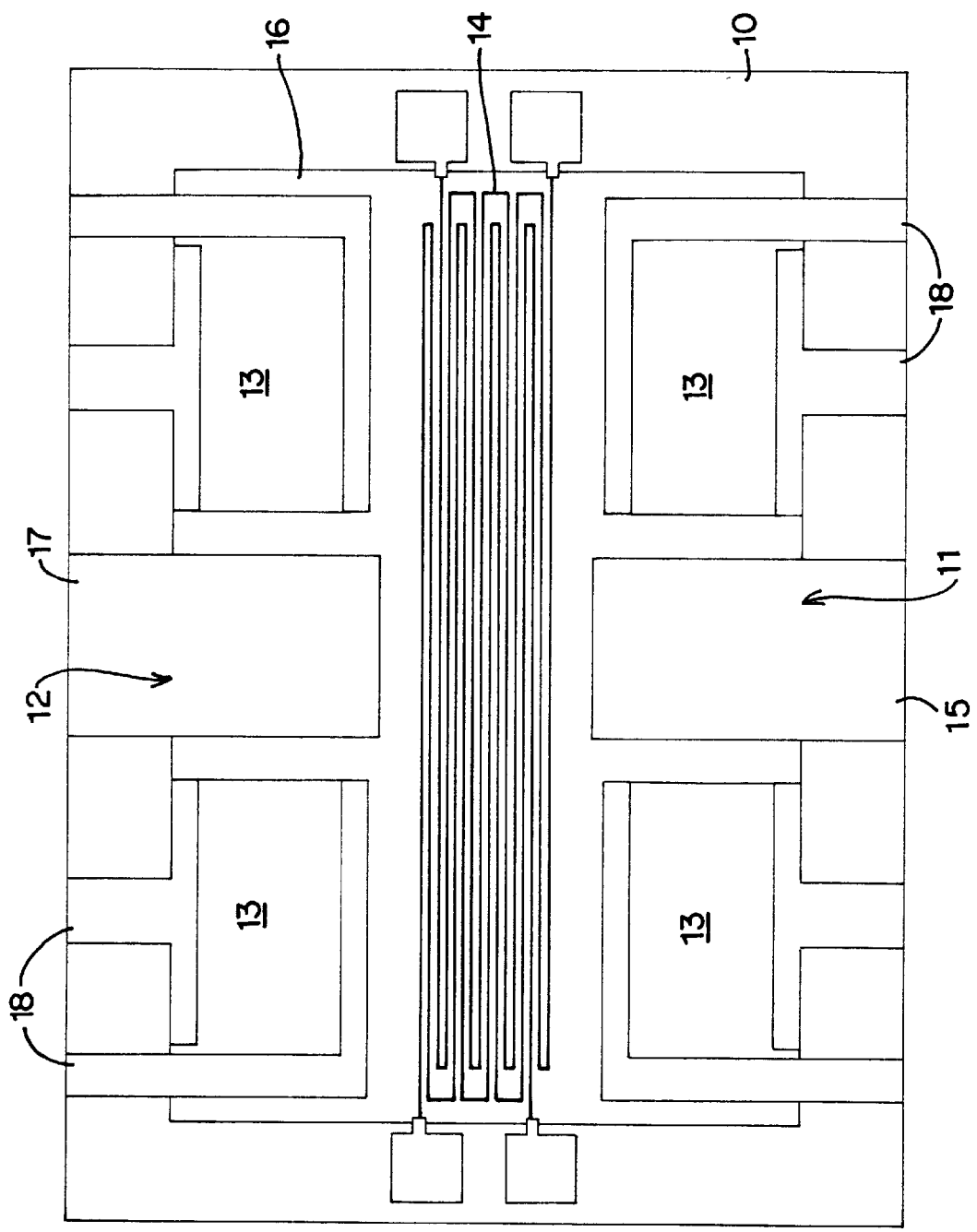
FIG. 5 illustrates the structure of the temperature matched dual delay line configuration of the present invention from the top view.

Referring now to FIG. 5, FIG. 6, and FIG. 7, a temperature compensated surface-launched acoustic wave sensor in accordance with the present invention is formed on a suitable substrate 10, such as a piezoelectric material, preferably selected from, but not limited to, the group of α-quartz, lithium niobate, and lithium tantalite, or a non-piezoelectric material coated with a layer which provides acousto-electric coupling, such as zinc oxide. In one embodiment of the invention, the substrate is 24° rotated Y-cut α-quartz; however, alternative substrate materials may be employed, provided such materials do not substantially adversely affect the general properties of the sensor as set out herein. Suitable substrates include, but are not limited to, lithium niobate and lithium tantalite.

Upon the substrate 10, interdigital transducers 13, referred to herein as IDTs, are deposed for the generation and reception of acoustic waves. The surface-launched acoustic wave mode can be chosen from the group including surface acoustic waves, surface skimming bulk waves, pseudo-surface acoustic waves, liquid guided acoustic waves, acoustic plate modes, Love waves, Lamb waves, and surface transverse waves. The IDTs 13 are configured in the dual delay line configuration from the prior art, including a reference delay line 11 and a sensing delay line 12. In one embodiment of the present invention, the IDTs are formed of aluminum between 50 and 200 nm thick. Again, alternative materials may be employed including, but not limited to, gold, silver, platinum, tungsten, and chromium. One or more serpentine resistive thermal devices 14, referred to herein as RTDs, may be deployed between delay lines 11 and 12 for the precise measurement of the surface temperature of the device. In one embodiment of the invention, the RTDs may be photolithographically etched from the same film as the IDTs and so, therefore, may be formed of aluminum between 50 and 200 nm thick or one of the other suitable materials identified.

Upon the delay path of the reference delay line 11 is deposed a chemically sensitive film 15. In one embodiment of the invention, this film is comprised of gold between 20 and 200 nm thick. The active areas of the IDTs 13, RTDs 14, and reference film 15 are coated with an inert dielectric material 16, referred to herein as the "passivation layer." In one embodiment of the invention, this film is formed of silicon dioxide between 100 and 500 nm thick. Alternatively, the passivation layer 16 may be formed silicon nitride or aluminum nitride, but not limited thereto.

A second sensing film 17 identical to the reference film 15 is deposed upon the sensing delay path on top of the passivation layer 16, such that it can be exposed to the gaseous or liquid environment in which the sensor is designed to operate, while the reference film 15 is isolated from that environment by the passivation layer 16. The sensing film may be created from any one of, or a combination of, metals, polymers, metal oxides, or biologically active materials any of which must have sufficient sensitivity to generate a response signal to be amplified. The sensing film may be formed of any suitable thickness, but is preferably between one and 1000 nanometers in thickness. Electrical connections to the IDTs 13 are made by extending the bus bars 18 outward from beneath the passivation layer 16.

Figure 8:
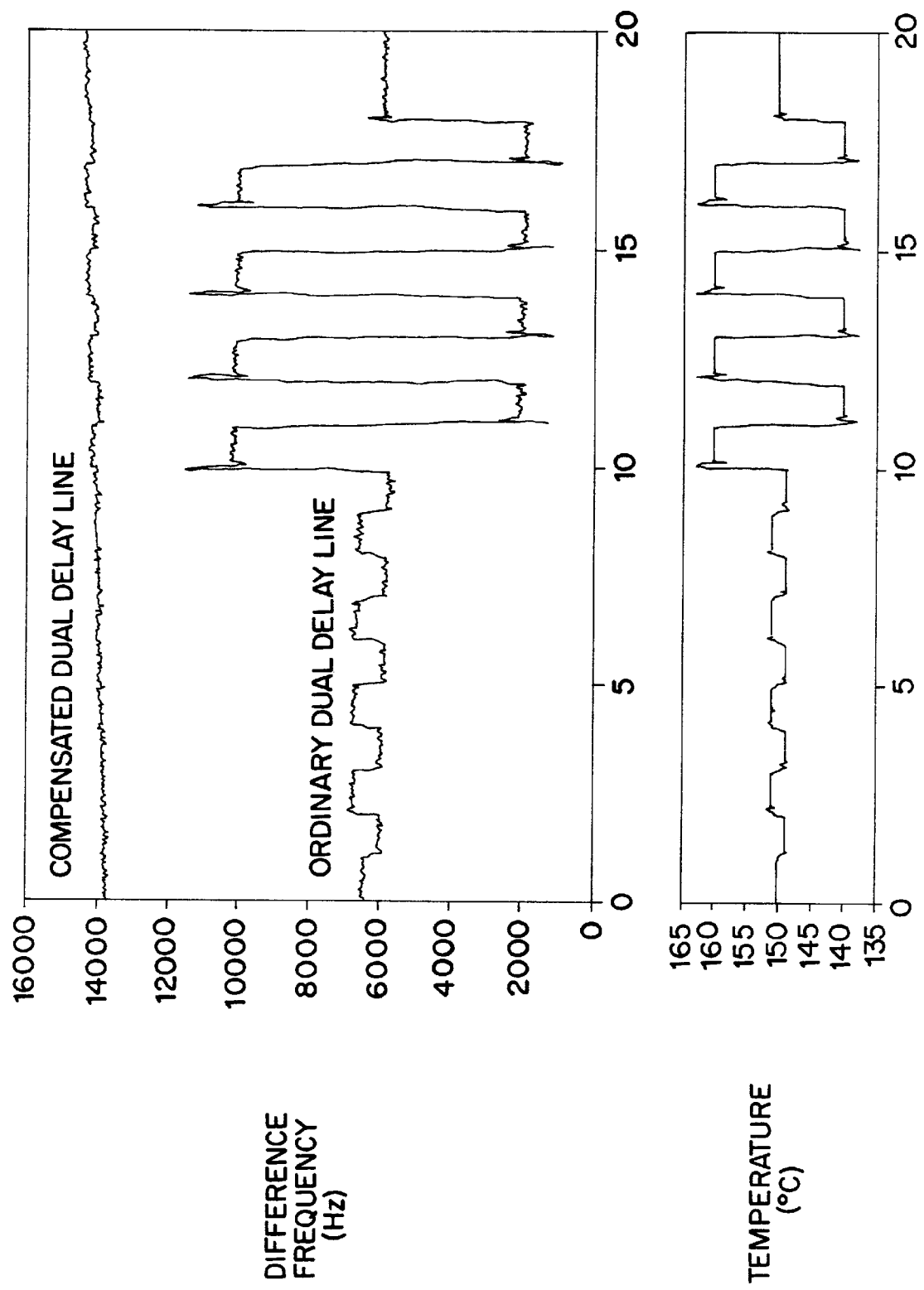
FIG. 8 plots the frequency stability of an ordinary dual delay line SAW device like those used in the prior art compared to one embodiment of the present invention for 150±1° C. and 150±10° C. temperature variations.

The temperature compensated surface-launched acoustic wave sensor in accordance with the present invention is used in the dual resonator or dual delay line oscillator configuration of the prior art. Because of the chemically passivated reference film 15 of the invention, however, precise temperature matching of the sensor channels and the reference channels, which channels refer either to delay lines or to resonators, can be achieved in a manner which has heretofore never been done. The degree of improvement in the frequency stability of the present invention is demonstrated in FIG. 8, where frequency is plotted as a function of time for the present invention and a dual delay line from the prior art, whereby the operating temperature of the devices is purposely fluctuated over a range of 140–160° C. As the figure demonstrates, stability is dramatically improved by the present invention over the prior art.

As is known by those skilled in the art of surface-launched acoustic wave devices, a number of changes to the embodiment presented herein may be used advantageously for various applications. For example, certain surface-launched acoustic wave modes, including Love waves and surface transverse waves, require a layer of material on the device surface to "trap" the acoustic energy to the surface. Naturally, the passivation layer 16 may be tailored to suit this need. Likewise, the IDT and RTD materials and thicknesses may be varied extensively within the scope of this invention, as well as the constituents and thickness of the sensing film. Additional materials, such as adhesion layers for the IDTs, RTDs, reference film, sensing film, or passivation layer, may be employed, as well. Likewise, the inert material of the passivation layer may be substituted with a semiconducting or chemically sensitive layer or a layer that is compatible with particular attachment chemistries for various applications, including biological sensors. Such alterations are well known to those skilled in the art.

Thus, although the invention has been shown and described with respect to the exemplary embodiments thereof, it should be obvious to those skilled in the art that the foregoing and various other changes, omissions and additions to the form and detail thereof may be made therein and thereto, without departing from the spirit and the scope of the invention.

What is claimed is:

1. A temperature matched surface-launched acoustic wave sensor comprising:

a piezoelectric substrate or a non-piezoelectric material coated with a layer which provides acousto-electric coupling, referred to herein as the substrate;

a plurality of surface-launched acoustic wave delay lines or surface-launched acoustic wave resonators;

at least one of said delay lines or resonators that are reference channels, to be used as frequency references to which the oscillation frequencies of the remainder of said delay lines or resonators that are sensing channels, are compared;

a plurality of amplifiers, one for each of said delay lines or resonators, each having an input and an output or a combined input and output, each of said delay lines or resonators connected from the output of a corresponding one of said amplifiers to the input thereof in a feedback relationship so as to form an oscillator, the output of which is at a natural frequency of the related one of said delay lines or resonators;

a plurality of substantially identical thin films, which are physically, chemically, biologically, or otherwise sensitive to one or more gaseous or liquid-born analytes, said films being deposed upon said delay lines or resonators;

a thin coating of material, referred to herein as the passivation layer, which is not sensitive to said analytes, configured such that said passivation layer covers said sensing films on said reference channels, blocking or impeding interaction of said sensing films and said analytes thereby, and is covered by said sensing films on said sensing channels, allowing interaction between said sensing films and said analytes thereby.

2. The temperature matched surface-launched acoustic wave sensor of claim 1, wherein said surface-launched acoustic wave mode is chosen from the group consisting of surface acoustic waves, surface skimming bulk waves, pseudo-surface acoustic waves, liquid guided acoustic waves, acoustic plate modes, Love waves, Lamb waves, and surface transverse waves.

3. The temperature matched surface-launched acoustic wave sensor of claim 1, wherein said substrate is chosen from the group consisting of quartz, lithium niobate, and lithium tantalite.

4. The temperature matched surface-launched acoustic wave sensor of claim 1, wherein each of said channels includes one or more interdigital transducers and wherein the material for said interdigital transducers is chosen from the group consisting of aluminum, gold, silver, platinum, tungsten, and chromium.

5. The temperature matched surface-launched acoustic wave sensor of claim 1, wherein a metal or semiconductor material is deposed upon said substrate to be used as a resistive thermal device for temperature measurement thereof.

6. The temperature matched surface-launched acoustic wave sensor of claim 4, wherein the material for said resistive thermal device is chosen from the group consisting of silicon aluminum, gold, silver, platinum, tungsten, and chromium.

7. The temperature matched surface-launched acoustic wave sensor of claim 4, wherein said passivation layer is extended to cover the entirety of the acoustically active area of said interdigital transducers, thereby blocking or impeding physical, chemical, biological, or other interaction between said interdigital transducers and the gaseous or liquid environment in which the device is operated, thereby reducing long-term drift of the oscillation frequency.

8. The temperature matched surface-launched acoustic wave sensor of claim 6, wherein the electrical contact to said interdigital transducers is facilitated by extending bus bars of said interdigital transducers out from beneath the coverage of said passivation layer.

9. The temperature matched surface-launched acoustic wave sensor of claim 1, wherein the material for said sensing films are chosen from the group consisting of metals, polymers, metal oxides, and biologically active materials.

10. The temperature matched surface-launched acoustic wave sensor of claim 1, wherein the thickness of said sensing film is between 1 and 1000 nm.

11. The temperature matched surface-launched acoustic wave sensor of claim 1, wherein the material for said passivation layer is chosen from the group consisting of silicon dioxide, silicon nitride, and aluminum nitride.

12. The temperature matched surface-launched acoustic wave sensor of claim 1, wherein said sensing film is further coated with additional layers of material to promote sensitive detection of said analytes.

13. The temperature matched surface-launched acoustic wave sensor of claim 12, wherein said additional layers of material are used to bind biological materials or analytes.

14. A temperature-matched surface-launched acoustic wave sensor for detecting one or more analytes comprising:
   a. a piezoelectric substrate having acousto-electric coupling means;
   b. a plurality of detection channels disposed on said piezoelectric substrate;
   c. one or more reference channels disposed on said piezoelectric substrate, wherein said at least one or more reference channels is used as a frequency reference to which oscillation frequencies of said plurality of detection channels are compared;
   d. a plurality of amplifiers corresponding in number to the number of said plurality of detection channels and said one or more reference channels, wherein each of said detection channels and said reference channels is coupled to its respective amplifier in a feedback relationship so as to form an oscillator thereby, wherein an output of each oscillator is a natural frequency of its respective channel;
   e. one or more substantially identical sensing films applied to each of said detection channels, wherein said one or more sensing films is sensitive to the one or more analytes to be detected, said films being deposed on said detection channels; and
   f. a passivation layer disposed on said one or more sensing films disposed on said one or more reference channels and disposed under said one or more sensing films on said plurality of detection channels, for blocking or impeding interaction of said one or more sensing films and said one or more analytes in the area of said one or more reference channels, and for allowing interaction between said one or more sensing films and said one or more analytes in the area of said plurality of detection channels.

15. The sensor of claim 14, wherein said plurality of detection channels and said one or more reference channels include one or more interdigital transducers.

16. The sensor of claim 15, wherein a material used to form said interdigital transducers is selected from the group consisting of aluminum, gold, silver, platinum, tungsten, and chromium.

17. The sensor of claim 16, further comprising a resistive thermal device disposed on said substrate.

18. The sensor of claim 17, wherein said resistive thermal device is a temperature measurement device formed from a material selected from the group consisting of silicon aluminum, gold, silver, platinum, tungsten, and chromium.

19. The sensor of claim 14, wherein said sensing films are formed of a material selected from the group consisting of metals, polymers, metal oxides, and biologically active materials.

20. The sensor of claim 14, wherein said passivation layer is formed from a material selected from the group consisting of silicon dioxide, silicon nitride, and aluminum nitride.

21. The sensor of claim 14, wherein said surface-launched acoustic wave mode is chosen from the group consisting of surface acoustic waves, surface skimming bulk waves, pseudo-surface acoustic waves, liquid guided acoustic waves, acoustic plate modes, Love waves, Lamb waves, and surface transverse waves.

22. The sensor of claim 14, wherein said substrate is chosen from the group consisting of quartz, lithium niobate, and lithium tantalite.

23. The sensor of claim 15, wherein said passivation layer is extended to cover the entirety of the acoustically active area of said interdigital transducers, thereby blocking or impeding physical, chemical, biological, or other interaction between said interdigital transducers and the gaseous or liquid environment in which the device is operated, thereby reducing long-term drift of the oscillation frequency.

24. The sensor of claim 23, wherein the electrical contact to said interdigital transducers is facilitated by extending bus bars of said interdigital transducers out from beneath the coverage of said passivation layer.

25. The sensor of claim 14, wherein the thickness of each of said one or more sensing films is between 1 and 1000 nm.

26. The sensor of claim 14, wherein each of said one or more sensing films is coated with additional layers of material to promote sensitive detection of said analytes.

27. The sensor of claim 26, wherein said additional layers of material are used to bind biological materials or analytes.

* * * * *